US012558371B2

(12) United States Patent
Zhao et al.

(10) Patent No.: US 12,558,371 B2
(45) Date of Patent: Feb. 24, 2026

(54) CHONDROITIN SULFATE POLYSACCHARIDE, AND SEMI-SYNTHETIC PREPARATION METHOD THEREFOR AND USE THEREOF

(71) Applicant: Institute of Materia Medica, Chinese Academy of Medical Sciences, Beijing (CN)

(72) Inventors: Zhehui Zhao, Beijing (CN); Pingsheng Lei, Beijing (CN); Lianqiu Wu, Beijing (CN); Shuang Yang, Beijing (CN); Wenjie Wang, Beijing (CN); Haijing Zhang, Beijing (CN); Xiang Li, Beijing (CN)

(73) Assignee: Institute of Materia Medica, Chinese Academy of Medical Sciences, Beijing (CN)

( * ) Notice: Subject to any disclaimer, the term of this patent is extended or adjusted under 35 U.S.C. 154(b) by 1082 days.

(21) Appl. No.: 17/436,675

(22) PCT Filed: Mar. 5, 2020

(86) PCT No.: PCT/CN2020/078075

§ 371 (c)(1),
(2) Date: Dec. 3, 2021

(87) PCT Pub. No.: WO2020/177749

PCT Pub. Date: Sep. 10, 2020

(65) Prior Publication Data

US 2022/0143074 A1 May 12, 2022

(30) Foreign Application Priority Data

Mar. 5, 2019 (CN) ........................ 201910163208.8

(51) Int. Cl.
*A61K 31/737* (2006.01)
*A61P 19/02* (2006.01)
*C08B 37/00* (2006.01)

(52) U.S. Cl.
CPC ........... *A61K 31/737* (2013.01); *A61P 19/02* (2018.01); *C08B 37/0069* (2013.01)

(58) Field of Classification Search
CPC .......................... A61K 31/737; C08B 37/0069
See application file for complete search history.

(56) References Cited

U.S. PATENT DOCUMENTS

| | | | |
|---|---|---|---|
| 5,008,253 A | 4/1991 | Casu et al. | |
| 5,314,876 A | 5/1994 | Lormeau et al. | |
| 5,384,398 A | 1/1995 | Lormeau et al. | |
| 10,259,889 B2 | 4/2019 | Minamisawa et al. | |
| 2003/0100534 A1* | 5/2003 | Zoppetti | C08B 37/0069 536/54 |
| 2018/0086853 A1 | 3/2018 | Minamisawa et al. | |

FOREIGN PATENT DOCUMENTS

| | | | |
|---|---|---|---|
| EP | 0340628 | A2 | 11/1989 |
| EP | 3279220 | A1 | 2/2018 |
| JP | H01318002 | A | 12/1989 |
| JP | 105271305 | A | 10/1993 |
| JP | 2000309537 | A | 11/2000 |
| JP | 2006327955 | A | 12/2006 |
| JP | 2012031123 | A | 2/2012 |
| JP | 2017048404 | A | 3/2017 |
| JP | 2022-531825 | | 7/2022 |
| WO | 2016150206 | A1 | 10/2016 |

OTHER PUBLICATIONS

Takagaki, The Journal of Biological Chemistry, vol. 277, No. 11, Issue of Mar. 15, pp. 8882-8889, 2002. (Year: 2002).*
European Patent Office, Extended European Search Report issued on Oct. 25, 2022, for corresponding European Patent Application No. 20765896.4.
Bartolucci et al., Inhibition of human leukocyte elastase by chemically and naturally oversulfated galactosaminoglycans, Carbohydrate Research, vol. 276, 1995, pp. 401-408.
Japanese Patent Office, Reasons for Rejection issued on Dec. 27, 2022, for corresponding Japanese Patent Application No. 2021-552974 (English translation provided).
Hori et al., Effects of Chondroitin Sulfate on Colitis Induced by Dextran Sulfate Sodium in Rats, The Japanese Journal of Pharmacology, 2001, vol. 83, pp. 155-160.
China National Intellectual Property Administration (ISA), Chinese-language and English translation of International Search Report and Written Opinion issued for International Patent Application No. PCT/CN2020/078075, dated Jun. 11, 2020.
Korean Patent Office, Office Action dated Apr. 17, 2024, for corresponding Korean Patent Application No. 10-2021-7031157 (English translation provided).
Office action issued on Mar. 5, 2025 of Japanese application No. 2023-196288 with translation.

* cited by examiner

*Primary Examiner* — Layla D Berry
(74) *Attorney, Agent, or Firm* — Duane Morris LLP

(57) ABSTRACT

The present invention relates to the technical field of medicine, in particular to a chondroitin sulfate polysaccharide, and a semi-synthetic preparation method therefor and the use thereof. A metal salt of the chondroitin sulfate polysaccharide provided by the present invention has an anti-inflammatory effect, and can be used for preparing a drug against inflammatory diseases. In particular, the metal salt of the chondroitin sulfate polysaccharide provided by the present invention has anti-inflammatory and bone-protecting effects, and can be used for preparing a drug against rheumatoid arthritis and for preparing a drug against osteoarthritis. The present invention provides a method for preparing the metal salt of the chondroitin sulfate polysaccharide, and the metal salt of the chondroitin sulfate polysaccharide with different degrees of sulfation can be obtained by semi-synthetic means in the present invention. The method is simple to operate and suitable for large-scale production.

10 Claims, 4 Drawing Sheets

CHONDROITIN SULFATE POLYSACCHARIDE, AND SEMI-SYNTHETIC PREPARATION METHOD THEREFOR AND USE THEREOF

PRIORITY CLAIM AND CROSS-REFERENCE

The present application is a National Stage Application, filed under 35 U.S.C. 371, of International Patent Application No. PCT/CN2020/078075, filed on Mar. 5, 2020, which claims for the priority of Chinese Application No. 201910163208.8, filed on Mar. 5, 2019, each of which is incorporated herein by reference in its entirety.

TECHNICAL FIELD

The present disclosure relates to the technical field of medicine, and in particular to a metal salt of chondroitin sulfate glycan, and a preparation method and use thereof.

BACKGROUND OF THE INVENTION

Chondroitin sulfate glycan (CS) is a straight-chain sulfated glycosaminoglycan (GAG), which is formed from glucose and galactosamine that are linked alternately via β (1→3) and β (1→4) glycosidic bonds, which are sulfated at positions 2 and 3 of glucuronic acid and positions 4 and 6 of galactosamine to various degree, thus producing 11 native subtypes, with specific structures shown as follows:

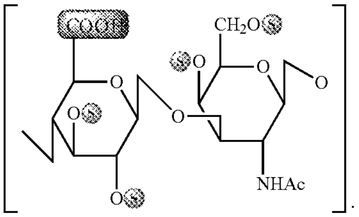

GlcA GalNAc

CS-O GlcA-GalNac
CS-A GlcA-GalNAc(4S)
CS-C GlcA-GalNAc(6S)
CS-D GlcA(2S)-GalNAc(6S)
CS-E GlcA-GalNAc(4S,6S)

CS-B Glc A(2S)-GalNAc(4S)
CS-R GlcA(2S,3S)-GalNAc
CS-T GlcA(2S)-GalNAc(4S,6S)
CS-M GlcA(3S)-GalNAc(4S,6S)
CS-K GlcA(3S)-GalNAc(4S)
CS-L GlcA(3S)-GalNAc(6S)

Chondroitin sulfate glycan, which widely exists in animals and is also a human endogenous substance, plays an important role in the physiological and pathological processes of nervous system, cancer, inflammation and the like by regulating the expression levels of various enzymes and factors.

At present, commercially available chondroitin sulfate glycan drugs and health products are all derived from cartilaginous tissue extracts of terrestrial animals, including type A and a small amount of type C. Chondroitin sulfate glycans derived from marine animals are different from those derived from terrestrial animals, and often mainly include subtypes such as type C (shark cartilage extracts) and type E (giant squid cartilage extracts). Studies have shown that chondroitin sulfate glycans of different compositions usually exhibit significantly different pharmacological activities. There remains a huge gap in the development of chondroitin sulfate glycan drugs with high pharmacological activities.

SUMMARY OF THE INVENTION

The technical problem solved by the present disclosure is to provide a metal salt of chondroitin sulfate glycan, and a method of preparation therefor and use thereof. The metal salt of chondroitin sulfate glycan provided in the present disclosure has superior pharmacological activities.

To solve the technical problem of the present disclosure, the present disclosure provides the following technical solutions.

The present disclosure provides a metal salt of chondroitin sulfate glycan (formula I), which is electrically neutral as a whole and include a chondroitin sulfate glycan anions and a metal cation.

(I)

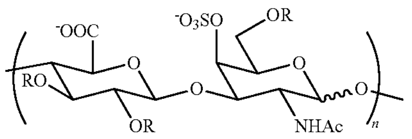

R = H or $SO_3^-$

The chondroitin sulfate glycan anion may have an average molecular weight of 1,000 Da to 15,000 Da.

The chondroitin sulfate glycan anion may have a molor ratio of $—SO_3^-$ to $—COO^-$ of 1.46 to 2.73. Preferably, the chondroitin sulfate glycan anion may have a molor ratio of $—SO_3^-$ to $—COO^-$ of 1.9 to 2.5.

The n for the chondroitin sulfate glycan anion may be within a range of 2≤n≤45.

Preferably, the chondroitin sulfate glycan anion may have an average molecular weight of 4,000 Da to 15,000 Da.

Preferably, the metal cation may comprise a sodium ion and/or a calcium ion or a potassium ion.

Preferably, the n for the chondroitin sulfate glycan anions may be within a range of 6≤n≤20.

In the present disclosure, the chondroitin sulfate glycan corresponding to the chondroitin sulfate glycan anion may mainly comprise chondroitin sulfate glycan C, chondroitin sulfate glycan E, chondroitin sulfate glycan A, and a balance of chondroitin sulfate glycans of other subtypes. Based on 100% of the chondroitin sulfate glycan by weight, the chondroitin sulfate glycan C, chondroitin sulfate glycan E, and chondroitin sulfate glycan A may preferably have a total content of 60% to 92% by weight. The chondroitin sulfate glycan C may preferably have a content of 0% to 30% by weight, more preferably, 10% to 25% by weight. The chondroitin sulfate glycan E may preferably have a content of 0% to 80% by weight, more preferably, 10% to 60% by weight. The chondroitin sulfate glycan A may preferably have a content of 0% to 90% by weight, more preferably, 0% to 70% by weight.

In the present disclosure, the chondroitin sulfate glycan anion may preferably have $—SO_3^-$ at a content of 14% to 27% by weight.

In the present disclosure, the chondroitin sulfate glycan anion may have alduronic acid preferably at a content of 20% to 35% by weight, and hexosamine preferably at a content of 22% to 32% by weight.

In the present disclosure, the metal cation preferably may comprise a sodium ion and/or a calcium ion and/or a potassium ion, more preferably, a sodium ion or a calcium ion.

In a second aspect, the present disclosure provides a method for preparation of the metal salt of chondroitin sulfate glycan as described in the first aspect, comprising the steps of:

- mixing a raw material of chondroitin sulfate glycan, a sulfating reagent, and an organic solvent for sulfation to provide a sulfation product system; and
- subjecting the sulfation product system successively to a first precipitating treatment, salification treatment, dialysis, a second precipitating treatment, and gel column purification to provide the metal salt of chondroitin sulfate glycan, wherein a salifying reagent used in the salification treatment is an aqueous metal hydroxide solution.

The raw material of chondroitin sulfate glycan comprises chondroitin sulfate glycan A and chondroitin sulfate glycan C, wherein the chondroitin sulfate glycan A may have a content of 70% to 90% by weight, and the chondroitin sulfate glycan C may have a content of 10% to 30% by weight. In the present disclosure, the raw material of chondroitin sulfate glycan used is purchased from Yantai Dongcheng pharmaceutical group Co., Ltd. The chondroitin sulfate glycan raw material has an average molecular weight of 20,000 Da to 23,000 Da, a molar ratio of $-SO_3^-$ to $-COO^-$ of 1, wherein the chondroitin sulfate glycan A has a content of 70% to 90% by weight, and the chondroitin sulfate glycan C has a content of of 10% to 30% by weight. The raw material of chondroitin sulfate glycan conforms to relevant requirements of standards in Chinese Pharmacopoeia (version 2015).

The raw material of chondroitin sulfate glycan may have an average molecular weight of 20,000 Da to 23,000 Da.

The raw material of chondroitin sulfate glycan may have a molar ratio of $-SO_3^-$ to $-COO^-$ of 0.9 to 1.1.

The sulfating reagent may comprise one or more selected from the group consisting of sulfur trioxide trimethylamine complex, sulfur trioxide pyridine complex, and sulfur trioxide triethylamine complex.

The equivalent ratio of the sulfating reagent to the repeating disaccharide units in the raw material of chondroitin sulfate glycan may be (1-10):1, more preferably, (3-8):1.

The sulfation may be performed at a temperature of 40° C. to 120° C. for 2 h to 36 h, more preferably, for 6 h to 24 h. In the present disclosure, the sulfation may be preferably performed under stirring. In the present disclosure, the stirring rate is not particularly limited, as long as a stirring rate well known to those skilled in the art may be employed.

The salifying reagent may be an aqueous sodium hydroxide solution and/or an aqueous potassium hydroxide solution. The salifying reagent may have a concentration of 1 mol/L to 4 mol/L.

A first precipitating reagent used in the first precipitating treatment may be an aqueous ethanol solution with a volume fraction of 90% to 95%.

A second precipitating reagent used in the second precipitating treatment may be ethanol.

A dialysis bag used in the dialysis may have a molecular weight cut-off of 3,000 Da to 12,000 Da.

In the present disclosure, adding mode, adding rate, and amount for adding the first precipitating reagent are not particularly limited, as long as the sulfation products in the sulfation product system can be precipitated completely. In the present disclosure, the first precipitating treatment may preferably be performed for 25 min to 35 min, and the first precipitating treatment may preferably be performed at room temperature under stirring.

In the present disclosure, after the first precipitating treatment is completed, the resulting system may preferably be filtered. The obtained filter cake may be dissolved in water. Then, the resulting solution may be mixed with the salifying reagent for salification treatment. In the present disclosure, a ratio of the amount of the water used for dissolving and the amount of the filter cake may preferably be (0.8-1.2) mL:1 g, more preferably, 1 mL:1 g. In the present disclosure, the salifying reagent may preferably be an aqueous sodium hydroxide solution and/or an aqueous potassium hydroxide solution, more preferably, an aqueous sodium hydroxide solution or an aqueous potassium hydroxide solution. The salifying reagent may preferably have a concentration of 1 mol/L to 4 mol/L, more preferably, 2 mol/L to 3 mol/L. If the salifying reagent is an aqueous sodium hydroxide solution and an aqueous potassium hydroxide solution, the concentration of the salifying reagent refers to the total concentration of sodium hydroxide and potassium hydroxide. In the present disclosure, adding amount of the salifying reagent is not particularly limited, preferably a neutral pH can be ensured for the system obtained by mixing the dissolved filter cake with the salifying reagent, as long as corresponding sodium salt and/or potassium salt may be obtained.

In the present disclosure, after the salification treatment is completed, the resulting solution may be dialyzed. A dialysis bag used in the dialysis may preferably have a molecular weight cut-off of 3,000 Da to 12,000 Da, more preferably, 8,000 Da to 12,000 Da. In the present disclosure, the dialysis may be performed preferably for 2 d to 3 d, more preferably, for 2 d. During the dialysis, water may preferably be refreshed once every 12 h.

In the present disclosure, after the dialysis is completed, the resulting system may preferably be subjected to rotary evaporation. The residue may be dissolved with an aqueous sodium acetate solution (an aqueous NaOAc solution). Then, the obtained solution may be mixed with ethanol for the second precipitating treatment. In the present disclosure, the aqueous NaOAc solution may preferably have a concentration of 2% to 5% by mass, more preferably, 2% to 3% by mass. In the present disclosure, the residue may be dissolved with an aqueous NaOAc solution to ensure that the residue may be dissolved in ethanol better, thereby facilitating the subsequent second precipitating treatment. In the present disclosure, the amount ratio between the residue, the aqueous NaOAc solution, and ethanol may be preferably 1 g:(8-12) mL:(3.5-4.5) mL, more preferably, 1 g:10 mL:4 mL.

In the present disclosure, after the second precipitating treatment is completed, the resulting system may preferably be centrifuged to provide a crude product of metal salt of chondroitin sulfate glycan as a solid. In the present disclosure, in order to ensure that the metal salt of chondroitin sulfate glycan finally obtained has a high purity, the crude product of metal salt of chondroitin sulfate glycan may preferably be subjected to the first precipitating treatment, the salification treatment, the dialysis, and the second precipitating treatment repeatedly, and the resulting crude product is subjected to a subsequent gel column purification. In the present disclosure, a gel column used in the gel column purification may preferably be a G25 gel column. The eluent used in the gel column purification may preferably be water.

In the present disclosure, after the gel column purification is completed, the resulting eluate may preferably be dried to provide the metal salt of chondroitin sulfate glycan. In the present disclosure, the drying may preferably be lyophilization. In the present disclosure, the temperature and the period for the lyophilization are not particularly limited, as long as the materials can be completely dried.

In a third aspect, the technical solution of the present disclosure provides a pharmaceutical composition, comprising the metal salt of chondroitin sulfate glycan as described in the first aspect and a pharmaceutically acceptable carrier. The pharmaceutical composition may be prepared by a method well known in the art. Any dosage forms suitable for human or animals may be formulated by combing the compound of the present disclosure with one or more pharmaceutically acceptable solid or liquid excipients and/or adjuvants. The compound of the present disclosure may usually have a content of 0.1% to 95% by weight in the pharmaceutical composition of the present disclosure.

The compound of the present disclosure or a pharmaceutical composition comprising the same may be administered at a unit dosage enterally or parenterally. The administration route may include oral administration, intravenous injection, intramuscular injection, subcutaneous injection, nasal administration, oral mucosal administration, ocular administration, pulmonary administration, respiratory administration, transdermal administration, vaginal administration, rectal administration, and the like.

A dosage form for administration may be a liquid dosage form, a solid dosage form, or a semisolid dosage form. The liquid dosage form may be a solution (including a true solution and a colloidal solution), an emulsion (including an o/w type, a w/o type, and a multiple emulsion), a suspension, an injection (including a water injection, a powder injection, and an infusion), an eye drop, a nose drop, a lotion, a liniment, or the like. The solid dosage form may be a tablet (including a conventional tablet, an enteric-coated tablet, a lozenge, a dispersible tablet, a chewable tablet, an effervescent tablet, and an orally disintegrating tablet), a capsule (including a hard capsule, a soft capsule, and an enteric-coated capsule), a granule, a powder, a pellet, a dropping pill, a suppository, a film, a patch, a gas (powder) aerosol, a spray, or the like. The semisolid dosage form may be an ointment, a gel, a paste, or the like.

The compounds of the present disclosure may be formulated into a normal preparation, a sustained-release preparation, a controlled-release preparation, a targeting preparation, and various particulate drug delivery systems.

In order to formulate the compounds of the present disclosure into tablets, various excipients well known in the art may be widely used, including a diluent, an adhesive, a wetting agent, a disintegrant, a lubricant, and a glidant. The diluent may be starch, dextrin, sucrose, glucose, lactose, mannitol, sorbitol, xylitol, microcrystalline cellulose, calcium sulphate, calcium hydrogen phosphate, calcium carbonate, or the like. The wetting agent may be water, ethanol, isopropanol, or the like. The adhesive may be starch paste, dextrin, syrup, honey, glucose water, microcrystalline cellulose, acacia mucilage, gelatin paste, sodium carboxymethylcellulose, methylcellulose, hydroxypropyl methylcellulose, ethylcellulose, acrylic resin, Carbomer, polyvinylpyrrolidone, polyethylene glycol, or the like. The disintegrant may be dry starch, microcrystalline cellulose, low-substituted hydroxypropylcellulose, crosslinked polyvinylpyrrolidone, crosslinked sodium carboxymethylcellulose, sodium carboxymethyl starch, sodium bicarbonate and citric acid, polyoxyethylene sorbitol fatty acid ester, sodium dodecyl sulfate, or the like. The lubricant and glidant may be talcum powder, silicon dioxide, stearate, tartaric acid, liquid paraffin, polyethylene glycol, or the like.

The tablet may be further formulated into a coated tablet, such as a sugar-coated tablet, a film-coated tablet, an enteric coated tablet, or a double-layer tablet and a multi-layer tablet.

In order to formulate an administration unit into capsules, the compounds of the present disclosure as the effective ingredients may be mixed with a diluent and a glidant, and the resulting mixture is then directly placed in hard capsules or soft capsules. Moreover, the compounds of the present disclosure as the effective ingredients may be first formulated into granules or pellets with a diluent, an adhesive, and a disintegrant, and then placed into hard capsules or soft capsules. Various diluents, adhesives, wetting agents, disintegrants, and glidants used for preparing tablets of the compounds of the present disclosure may also be used for preparing capsules of the compounds of the present disclosure.

In order to formulate the compounds of the present disclosure into an injection, water, ethanol, isopropanol, and propylene glycol, or a mixture thereof may be used as a solvent, and an appropriate amount of a solubilizer, a cosolvent, a pH regulator, and an osmotic pressure regulator commonly used in the art can be added. The solubilizer or cosolvent may be poloxamer, lecithin, hydroxypropyl-β-cyclodextrin, or the like. The pH regulator may be phosphate, acetate, hydrochloric acid, sodium hydroxide, or the like. The osmotic pressure regulator may be sodium chloride, mannitol, glucose, phosphate, acetate, or the like. In order to prepare a lyophilized powder injection, mannitol, glucose, or the like may also be added as a proppant.

Furthermore, if desired, a coloring agent, a preservative, a perfume, a corrigent, or other additives may also be added into the pharmaceutical preparations.

In order to achieve the medication purpose and enhance the therapeutic effect, the drugs or pharmaceutical compositions of the present disclosure may be administered by any well-known administration route.

The administration dosage of the compound or pharmaceutical composition of the present disclosure may vary in a large range according to the nature and severity of diseases to be prevented or treated, the individual characteristics of patients or animals, the administration routes and dosage forms, and the like. In general, the compounds of the present disclosure may have an appropriate daily dosage within a range of 0.001 to 150 mg/Kg body weight, preferably, 0.1 to 100 mg/Kg body weight, more preferably, 1 to 60 mg/Kg body weight, and most preferably, 2 to 30 mg/Kg body weight. The above dosage may be applied in one dosage unit or divided into several dosage units, which depends on clinical experiences of physicians and administration regimens involving the use of other therapeutic means.

The compound or composition of the present disclosure may be administered either at alone, or in combination with other therapeutic drugs or symptomatic drugs. In a situation that there is a synergistic effect between the compound of the present disclosure and other therapeutic drugs, a dosage of the compound should be adjusted according to actual conditions.

In a fourth aspect, the present disclosure provides use of the metal salt of chondroitin sulfate glycan as described in the first aspect of the present disclosure in the preparation of a medicament for treating an inflammatory disease. The inflammatory disease may include osteoarthritis and rheumatoid arthritis.

The present disclosure provides a metal salt of chondroitin sulfate glycan, which play a role of anti-inflammation by inhibiting both the NF-κB signaling pathway and the expression and functions of inflammation-associated factors and enzymes. As shown in the results of the Examples, the metal salt of chondroitin sulfate glycan provided in the present disclosure has an anti-inflammatory effect, and thus can be used in the preparation of a medicament for treating an inflammatory disease.

The present disclosure provides a metal salt of chondroitin sulfate glycan, which not only has an anti-inflammatory activity, but also has an effect of improving bone density. As shown in the results of the Examples, the metal salt of chondroitin sulfate glycan provided in the present disclosure has the effects of anti-inflammation and bone protection, and thus can be used in the preparation of a medicament for treating a disease of rheumatoid arthritis.

The present disclosure provides a metal salt of chondroitin sulfate glycan, which can increase water content in cartilages and has a cartilage protection effect. As shown in the results of the Examples, the metal salt of chondroitin sulfate glycan provided in the present disclosure has the effects of anti-inflammation and cartilage protection, and thus can be used in the preparation of a medicament for treating a disease of osteoarthritis.

Beneficial technical effects: The compound of the present disclosure has a prominent anti-inflammatory activity in vivo, which exceeds that of naturally derived CS-E, as it has a high sulfation degree (a ratio of sulfate to carboxylate is within a specific range). The sulfation degree of the compound in the present disclosure has a significant structure-activity relationship (SAR) with the anti-inflammatory activity in vivo. In an animal model of acute ulcerative proctitis, the compound of the present disclosure also exhibits its outstanding biological activity and significant therapeutic effects. As Compared to naturally derived CS-A and CS-E, the compound of the present disclosure shows prominent biological activity and significant therapeutic effect in both anti-type I collagen-induced toe swelling (RA) animal models and papain-induced arthritis (OA) rat models.

The present disclosure provides a method for preparation of the metal salt of chondroitin sulfate glycan. In the present disclosure, the metal salt of chondroitin sulfate glycan with various sulfation degree can be obtained through a semi-synthesis procedure, which is simple and suitable for large-scale production.

BRIEF DESCRIPTION OF THE DRAWINGS

In FIG. 8, the CON group shows a normal joint space, an intact and undamaged articular cartilage surface, a normal subchondral bone, a normal cartilage thickness, an appropriate amount of subpatellar fat, a synovial membrane, and a little synovial fluid; the MOD group shows a narrowed joint space, a damaged or even lost articular cartilage surface, an incomplete outer cartilage edge, an unclear cartilage shape, and a decreased cartilage thickness; and the 5H group shows a clear joint shape, a restored joint space, and a little synovial fluid.

In FIG. 9, the CON group shows the shape of the knee joints of normal rats; the MOD model group shows the bone destruction and severe erosion in the subchondral bone of the knee joints, the formation of obvious cavities at the joints, and the deformation of bone joints; the POS positive drug and 5L groups show less bone destruction and erosion than the model group; and the 5M and 5H groups show significantly improved bone destruction and erosion as compared with the model group.

DETAILED DESCRIPTION OF THE INVENTION

Example 1

Figure 1:
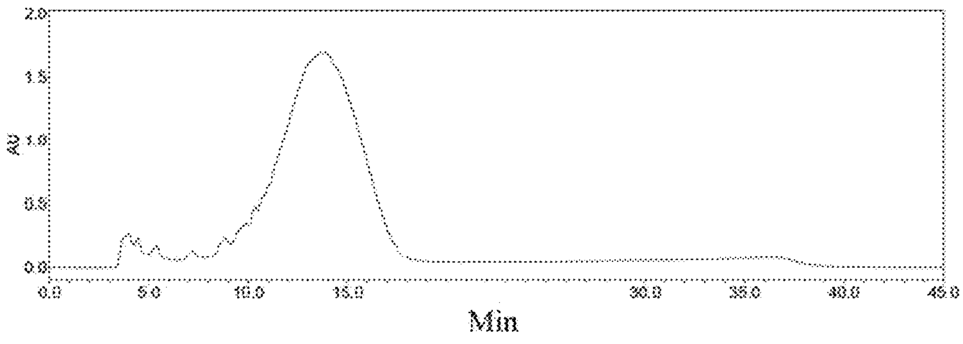
FIG. 1 is a high performance liquid chromatogram of Glycan 1 prepared in Example 1.
Figure 2:
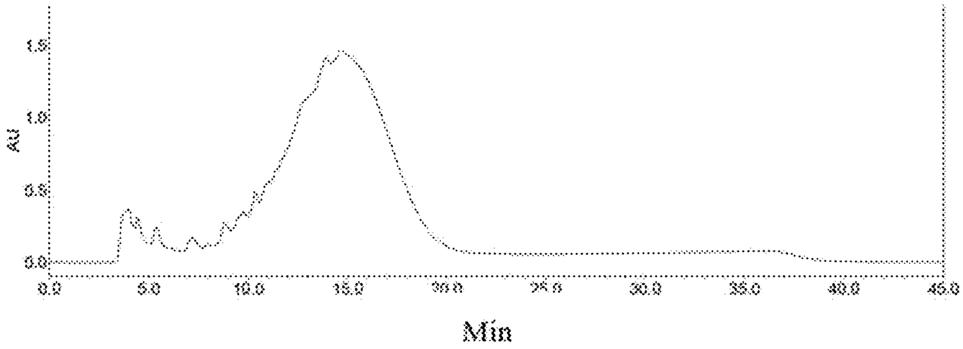
FIG. 2 is a high performance liquid chromatogram of Glycan 2 prepared in Example 2.
Figure 3:
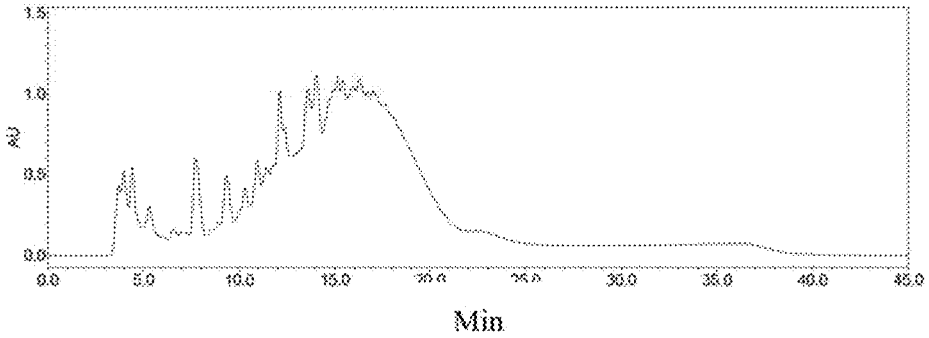
FIG. 3 is a high performance liquid chromatogram of Glycan 3 prepared in Example 3.
Figure 4:
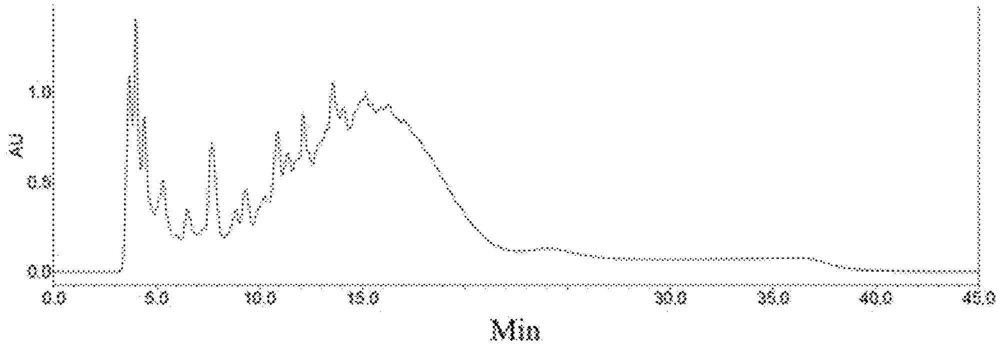
FIG. 4 is a high performance liquid chromatogram of Glycan 4 prepared in Example 4.

(1) 26.8 g of commercially available glycan chondroitin sulfate A (Yantai Dongcheng pharmaceutical group Co., Ltd., NO. CSJ1170701) was dissolved in 360 mL of dimethyl sulfoxide. Then, 24 g of sulfur trioxide trimethylamine complex (3 eq.) was added. The resulting mixture was reacted at 50° C. under stirring for 6 h.

(2) The resulting reaction system was cooled to room temperature. Then, 400 mL of an aqueous ethanol solution with a volume fraction of 95% was added. The resulting mixture was stirred for 30 min, and then filtered. The resulting filter cake was dissolved with water (the ratio of the amount of water to the amount of the filter cake was 1 mL:1 g). The pH value was adjusted to 7.0 with a 2 mol/L aqueous NaOH solution. The resulting solution was put into a dialysis bag (with a molecular weight cut-off of 12,000 Da) for a dialysis of 2 d. Then, the resulting dialysate was subjected to rotary evaporation to provide a solid.

(3) The obtained solid was dissolved in an aqueous NaOAc solution at a concentration of 2% by mass. Then, absolute ethanol was added. The resulting mixture was subjected to sufficient precipitation and then centrifuged to give a crude product; wherein the ratio between the amount of the solid, the amount of aqueous NaOAc solution, and the amount of absolute ethanol was 1 g: 10 mL:40 mL.

(4) The obtained crude product was subjected to step (2) and step (3) once again. Then, the resulting product was purified on a G25 gel column ($H_2O$ was used as an eluent). Finally, the resulting eluate was lyophilized to give 21.3 g of a sodium salt of chondroitin sulfate glycan (referred to as Glycan 1).

Example 2

4.4 g of a sodium salt of chondroitin sulfate glycan (referred to as Glycan 2) was prepared according to the steps in Example 1, except that, in step (1), 6.7 g of commercially available glycan chondroitin sulfate A was dissolved in 90 mL of dimethyl sulfoxide, then 8 g of sulfur trioxide trimethylamine complex (4 eq.) was added; and the resulting mixture was reacted at 60° C. under stirring for 24 h.

Example 3

4.1 g of a sodium salt of chondroitin sulfate glycan (referred to as Glycan 3) was prepared according to the steps in Example 1, except that, in step (1), 6.7 g of commercially available chondroitin sulfate glycan A was dissolved in 90 mL of dimethyl sulfoxide, then 10 g of sulfur trioxide trimethylamine complex (5 eq.) was added; the resulting mixture was reacted at 60° C. under stirring for 24 h; and the dialysis bag had a molecular weight cut-off of 7,000 Da.

Example 4

3.9 g of a sodium salt of chondroitin sulfate glycan (referred to as Glycan 4) was prepared according to the steps in Example 1, except that, in step (1), 6.7 g of commercially available chondroitin sulfate glycan A was dissolved in 90 mL of dimethyl sulfoxide, then 12 g of sulfur trioxide trimethylamine complex (6 eq.) was added, and a resulting mixture reacted at 70° C. for 20 h under stirring; and the dialysis bag had a molecular weight cut-off of 5,000 Da.

Example 5

1.0 g of a sodium salt of chondroitin sulfate glycan (referred to as Glycan 5) was prepared according to the steps in Example 1, except that, in step (1), 1.0 g of commercially available chondroitin sulfate glycan A was dissolved in 13 mL of dimethyl sulfoxide, then 2.4 g of sulfur trioxide trimethylamine complex (8 eq.) was added; the resulting mixture was reacted at 100° C. under stirring for 36 h; and the dialysis bag had a molecular weight cut-off of 3,500 Da.

Pharmacological Experiments

Experimental Example 1

The compositions of the glycans 1 to 5 prepared in Examples 1 to 5 were analyzed, including an average molecular weight (Da), $-SO_3^-/-COO^-$ (a molar ratio), contents of $-SO_3^-$, alduronic acid, and hexosamine, an anticoagulation titer (IU), a content of degradable glycans, and proportions of ingredients of each subtype (the Glycans 1 to 5 prepared in Examples 1 to 5 were degraded with chondroitin sulfate ABC enzymes, and ingredients of each subtype were tested by high performance liquid chromatography, specifically referring to the proportions of chondroitin sulfate A, chondroitin sulfate C, and chondroitin sulfate E, wherein the Glycans 1 to 5 further contain a balance of chondroitin sulfate glycans of other subtypes, which were not further specified herein. The high performance liquid chromatograms of the Glycans 1 to 4 were shown in FIG. 1 to FIG. 4). The specific results were shown in Table 1.

TABLE 1

Analysis results of the compositions of the Glycans 1 to 5 prepared in Examples 1 to 5

| Glycan type | $-SO_3^-$ content | $-SO_3^-/-COO^-$ | Average molecular weight | IU | Degradable glycan content | Proportions of C/A/E | Alduronic acid content | Hexosamine content |
|---|---|---|---|---|---|---|---|---|
| Glycan 1 | 14.17 | 1.46 | 14414 | <2.8 | 74.3 | 14.1/66.2/11.1 | 34.5 | 31.6 |
| Glycan 2 | 16.43 | 2.11 | 12956 | <2.8 | 66.3 | 16.3/47.4/22.4 | 31.4 | 25.9 |
| Glycan 3 | 23.85 | 2.20 | 5895 | <2.8 | 44.9 | 15.8/4.6/52.0 | 24.3 | 23.0 |
| Glycan 4 | 26.77 | 2.58 | 4848 | <2.8 | 26.0 | 16.6/0.0/44.9 | 20.7 | 22.4 |
| Glycan 5 | — | 2.73 | 4656 | <2.8 | 3.3 | — | — | — |

Experimental Example 2

Anti-inflammatory effects of the glycans 1 to 5 prepared in Examples 1 to 5 were evaluated, specifically as follows:

(1) Test method: experiments for evaluating pharmacodynamic activities of CS compounds in mouse ear acute swelling inflammation models caused by croton oil Animals: Balb/c mice, male (20 g to 22 g); 8 mice per group.

Groups: model group, positive drug (indometacin) group (5 mg/kg), natural extract (CS-E) group (200 mg/kg), and glycan groups (200 mg/kg, 100 mg/kg, and 50 mg/kg). Each of the positive drug and the compounds of CS series was formulated with sodium carboxymethylcellulose at a concentration of 0.5% by mass, and stored in a refrigerator at 4° C.

Administration and test: the mice were administered for 3 d, once a day. After the last administration, an induction rate on mouse ear swelling (%) and an inhibition rate on the ear swelling degree (%) by the compounds were calculated.

Statistical analysis: the experimental results were all expressed as "mean±standard deviation". A statistical difference between two groups was calculated and analyzed by the t-test method. * represents $p<0.05$, and ** represents $p<0.01$.

(2) The anti-inflammatory effects of glycans were shown in Tables 2 to 4.

TABLE 2

Anti-inflammatory effects of the glycans

| Group | Number of cases End/Start | Swelling rate (%) Mean ± SD | Inhibition rate (%) |
|---|---|---|---|
| Model group (croton oil) | 8/8 | 94.95 ± 18.42 | 0.00 |
| Indometacin group (5 mg/kg) | 8/8 | 70.25 ± 20.97* | 26.01 |
| Glycan 1 (200 mg/kg) | 8/8 | 89.94 ± 25.35 | 5.33 |
| Glycan 3 (200 mg/kg) | 8/8 | 56.13 ± 11.24* | 40.92 |

TABLE 3

Anti-inflammatory effects of the glycans

| Group | Number of cases End/Start | Swelling rate (%) Mean ± SD | Inhibition rate (%) |
|---|---|---|---|
| Model group (croton oil) | 8/8 | 102.96 ± 1.25 | 0.00 |
| Indometacin group (5 mg/kg) | 8/8 | 74.43 ± 20.97* | 27.70 |

TABLE 3-continued

Anti-inflammatory effects of the glycans

| Group | Number of cases End/Start | Swelling rate (%) Mean ± SD | Inhibition rate (%) |
|---|---|---|---|
| Natural extract chondroitin sulfate glycan-E (200 mg/kg) | 8/8 | 88.87 ± 17.49 | 12.87 |
| Glycan 3 (200 mg/kg) | 8/8 | 63.59 ± 29.51* | 37.66 |
| Glycan 4 (200 mg/kg) | 8/8 | 73.47 ± 13.92* | 27.97 |

TABLE 4

Anti-inflammatory effects of the glycans

| Group | Number of cases End/Start | Swelling rate (%) Mean ± SD | Inhibition rate (%) |
|---|---|---|---|
| Model group (croton oil) | 8/8 | 76.92 ± 8.07 | 0.00 |
| Indometacin group (5 mg/kg) | 8/8 | 45.34 ± 6.92* | 41.06 |
| Glycan 3 (200 mg/kg) | 8/8 | 28.38 ± 5.61** | 63.10 |
| Glycan 3 (100 mg/kg) | 8/8 | 40.58 ± 11.09* | 47.24 |
| Glycan 3 (50 mg/kg) | 8/8 | 20.55 ± 6.63** | 73.28 |
| Glycan 2 (200 mg/kg) | 8/8 | 54.56 ± 11.65 | 29.06 |
| Glycan 5 (200 mg/kg) | 8/8 | 47.52 ± 10.07* | 38.21 |

It can be seen from Tables 2 to 4 that there was a structure-activity relationship between sulfation degree of the glycans 1 to 5 and the anti-inflammatory activity. The glycans 2 to 5 exhibited prominent anti-inflammatory effects on mouse ear swelling models, which were superior to that of naturally derived CS-E glycan. In particular, the Glycan 3 exhibited a significant anti-inflammatory effect at a concentration throughout a range of 50 mg/kg to 200 mg/kg, with a significant dose-dependent relationship.

Experimental Example 3

Pharmacodynamics of the Glycan 3 (referred to as SEMI5) prepared in Example 3 was evaluated on anti-DSS models, specifically as follows:

I. Materials and Methods

1. Experimental Animals

C57BL/6J mice, male (18 g to 20 g), 6 mice per group, which were purchased from Beijing Huafukang Biotechnology Co., Ltd., with a license No.: SCXK (Beijing) 2014-0004.

2. Experimental Groups (1) Normal control group (control group): intragastrically administered with sodium carboxymethylcellulose at a concentration of 0.5% by mass.

(2) UC (Ulcerative colitis) model group (model group): intragastrically administered with sodium carboxymethylcellulose at a concentration of 0.5% by mass.

(3) SASP (a positive drug salazosulfapyridine) group: Shanghai Xinyi Pharmaceutical Co., Ltd. (Batch No.: 036151102), 500 mg/kg, which was formulated with sodium carboxymethylcellulose at a concentration of 0.5% by mass and stored at 4° C., and intragastrically administered once a day.

(4) SEMI5-50 group: 50 mg/kg, which was formulated with distilled water and stored at 4° C., and intragastrically administered once a day.

(5) SEMI5-150 group: 150 mg/kg, which was formulated with distilled water and stored at 4° C., and intragastrically administered once a day.

3. Experimental method After being adaptively raised for one week in an SPF animal house (experimental animal use license No.: SYXK (Beijing) 2014-0023), the C57BL/6J mice were randomly divided into 5 groups according to the above protocols. Mice in the UC model group and administration groups were modeled with DSS (MP, CA9011-18-1, US) every day according to the modeling method for ulcerative colitis that had been established in the laboratory. The normal control group (control group) and UC model group (model group) were intragastrically administered with sodium carboxymethylcellulose at a concentration of 0.5% by mass once a day. The SASP group, SEMI5-50 group, and SEMI5-150 group were intragastrically administered once a day according to the experimental protocols in the section of "Experimental groups". 7 d after modeling, typical UC pathological changes such as obvious listlessness, activity reduction, weight loss, watery stool, and hematochezia occurred in animals of the UC model group. The experiments were terminated, and animals in each group were sacrificed. Each of evaluation indexes related with colitis was detected (as shown in the subsequent section of experimental results). The anti-UC pharmacodynamic activity of each of the compounds was evaluated comprehensively.

II. Experimental Results

1. Effect of SEMI5 at each concentration on the body weight of DSS-induced UC model mice (Table 5 and FIG. 5).

TABLE 5

Data of change in body weight of UC mice in different groups

| Group | Number of cases End/Start | Body weight (g) X ± SD Start | End | Change in body weight (%) |
|---|---|---|---|---|
| Normal control group | 6/6 | 21.12 ± 1.33 | 22.25 ± 2.21 | ↑5.14 |
| UC model group | 6/6 | 21.97 ± 1.42 | 18.41 ± 1.82 | ↓16.17## |
| SASP group | 6/6 | 21.97 ± 0.71 | 18.76 ± 1.09 | ↓14.55 |
| SEMI5-50 (50 mg/kg) | 6/6 | 21.46 ± 0.71 | 19.52 ± 1.21 | ↓9.09* |
| SEMI5-150 (150 mg/kg) | 6/6 | 21.72 ± 0.88 | 18.68 ± 1.04 | ↓13.92 |

$p < 0.01$ vs. Con;
*$p < 0.05$ vs. Mod

Figure 5:
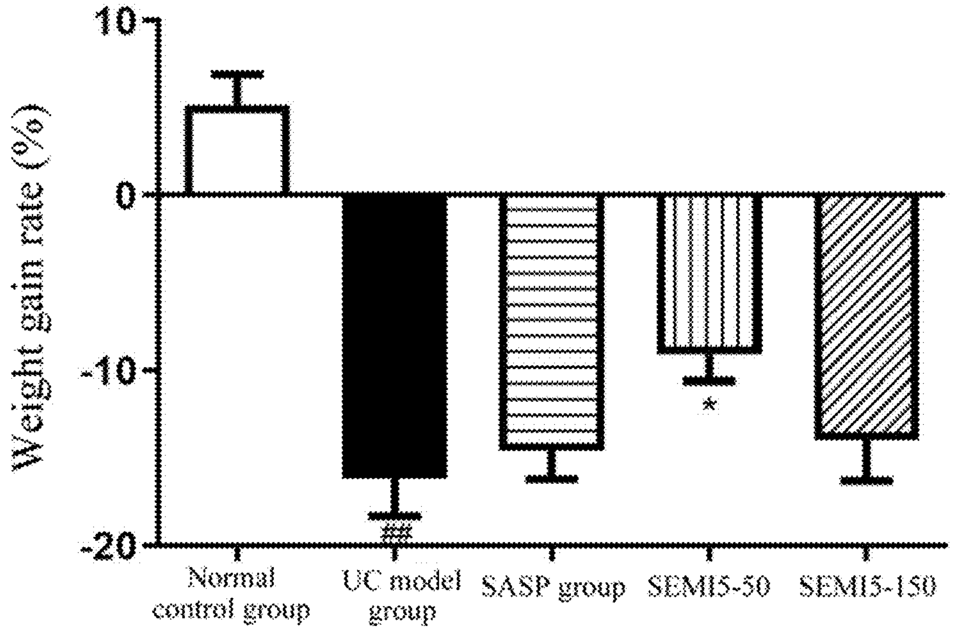
FIG. 5 is a comparison diagram of change in body weight of UC mice in different groups in Experimental Example 3. Note: ##p<0.01 vs. Con; and *p<0.05 vs. Mod.

It can be seen from Table 5 and FIG. 5 that, as compared with mice in the normal control group, the mice in the UC model group had a significantly reduced body weight with statistically significant difference, indicating the success of UC modeling. The SASP group and the SEMI5-150 group failed to effectively alleviate the body weight reduction of DSS-induced acute UC C57 BL/6J mice, while the SEMI5-50 group effectively alleviated the body weight reduction as compared with the UC model group, with statistically significant difference.

2. Effect of SEMI5 at each concentration on colon contracture of UC mice (Table 6 and FIG. 6).

TABLE 6

Comparative data of colon contracture of UC mice among different groups

| Group | Number of cases End/Start | Colon length (cm) | Colon contracture percentage (%) |
|---|---|---|---|
| Normal control group | 6/6 | 7.71 ± 0.59 | 0 |
| UC model group | 6/6 | 4.76 ± 0.54## | 38.26## |
| SASP group | 6/6 | 5.29 ± 0.61 | 31.39 |
| SEMI5-50 (50 mg/kg) | 6/6 | 5.66 ± 0.68* | 26.59* |
| SEMI5-150 (150 mg/kg) | 6/6 | 5.70 ± 0.94* | 26.07* |

p < 0.01 vs. Con;
*p < 0.05 vs. Mod

Figure 6:
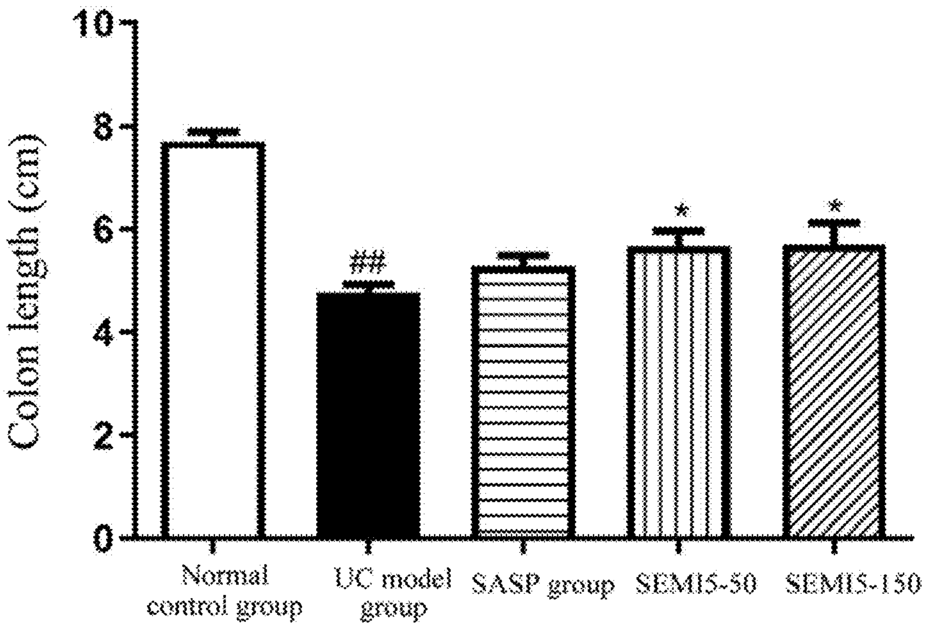
FIG. 6 is a comparison diagram of colon lengths of UC mice in different groups in Experimental Example 3. Note: ##p<0.01 vs. Con; and *p<0.05 vs. Mod.

It can be seen from Table 6 and FIG. 6 that, on the DSS-induced C57 BL/6J acute UC animal models, as compared with the normal control group, the UC model group exhibited a significantly reduced colon contracture, with statistically significant difference. The SASP group failed to effectively alleviate the colon contracture in the model animals. However, the SEMI5-50 group and the SEMI5-150 group can effectively alleviate the colon contracture as compared with the UC model group, with statistically significant difference.

3. Effect of SEMI5 at each concentration on the disease complex index DAI scores of UC mice (Table 7 and FIG. 7).

TABLE 7

Comparative data of DAI and composite index inhibition rate among different groups

| Group | Number of cases End/Start | Disease activity index DAI | DAI complex index inhibition rate (%) |
|---|---|---|---|
| Normal control group | 6/6 | 0.27 ± 0.14 | — |
| UC model group | 6/6 | 3.63 ± 0.46## | 0 |
| SASP group | 6/6 | 3.10 ± 0.59* | 14.68* |
| SEMI5-50 (50 mg/kg) | 6/6 | 1.87 ± 0.38** | 48.62** |
| SEMI5-150 (150 mg/kg) | 6/6 | 2.67 ± 0.62** | 26.61** |

p < 0.01 vs. Con;
**p < 0.01,
*p < 0.05 vs. Mod

Figure 7:
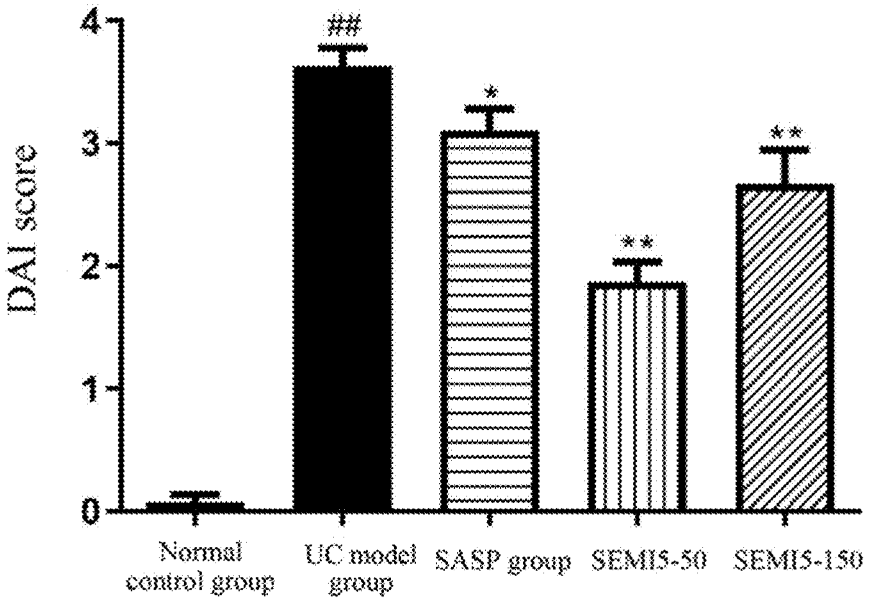
FIG. 7 is a comparison diagram of disease activity index (DAI) scores of mice in different groups in Experimental Example 3. Note: ##p<0.01 vs. Con; and **p<0.01, *p<0.05 vs. Mod.

It can be seen from Table 7 and FIG. 7 that, as compared with mice in the normal control group, the mice in the UC model group had a significantly increased disease complex index DAI, with statistically significant difference, indicating the success of modeling. Compared with the UC model group, the SEMI5-50 group and the SEMI5-150 group could significantly reduce the scores of disease complex index DAI of experimental animals, with statistically significant difference. The SASP group was improved to some extent, with statistically significant difference. The animals were evaluated by the DAI scores in terms of indexes such as animal body weight loss, stool property, hematochezia. The lower the DAI score was, the closer was the condition of the animal to a normal physiological status. The criteria for DAI scoring were shown in Table 8.

TABLE 8

DAI scoring criteria

| Score | Percentage of body weight loss (%) | Stool property | Hematochezia severity |
|---|---|---|---|
| 0 | 0 | normal | normal |
| 1 | 1~ | loose (+) | Occult blood positive (+) |
| 2 | 5~ | loose (++) | Occult blood positive (++) |
| 3 | 10~ | watery (+) | gross hematochezia (+) |
| 4 | >15 | watery (++) | gross hematochezia (++) |

Notes:
① Normal stools: formed stools;
② loose stools: pasty and half-formed stools inadherent to anus;
③ watery stools: water-like stools.

Experimental Example 4

The Glycan 3 (referred to as SEMI5) prepared in Example 3 was evaluated on anti-type I collagen-induced toe swelling mouse models, specifically as follows:

I. Materials and Methods

1. Animals. DBAI mice, male (20 g to 22 g); 7 mice per group.

2. Groups: blank control group, model group, positive drug indomethacin group (5 mg/kg), CSA group (200 mg/kg), CSE group (200 mg/kg), CS-E-semi3 group (200 mg/kg), and CS-Semi-5 group (200 mg/kg). Each of the positive drug and the compounds of CS series was formulated with 0.5% sodium carboxymethylcellulose, and stored in a refrigerator at 4° C.

3. Administration frequency: the mice were administered for 3 d, once a day.

4. Experimental method: according to an established method in the laboratory, after primary immunization, the body weight was measured every week for mice in each group. After the secondary shock immunization on day 21 of the experiment, the joint swelling degree was observed every week for mice in each group and the joint swelling index scoring was scored.

5. Statistical analysis: the experimental results were all expressed as "mean±standard deviation". A statistical difference between two groups was calculated and analyzed by the t-test method. * represents p<0.05, and ** represents p<0.01.

II Experimental Results

TABLE 9

Effects of different drugs on the body weight of mice

| Group | Number of cases End/Start | 3 | 4 | 5 | 6 | 7 |
|---|---|---|---|---|---|---|
| Normal control group | 7/7 | 21.61 ± 0.42 | 22.26 ± 0.40 | 23.21 ± 0.43 | 22.93 ± 0.45 | 23.76 ± 0.54 |
| CIA model group | 6/7 | 20.55 ± 0.61 | 19.73 ± 0.98# | 20.05 ± 1.06# | 19.48 ± 0.96## | 19.76 ± 0.61## |

TABLE 9-continued

Effects of different drugs on the body weight of mice

| Group | Number of cases End/ Start | 3 | 4 | 5 | 6 | 7 |
|---|---|---|---|---|---|---|
| Positive drug group (0.25 mg/kg) | 7/7 | 22.11 ± 0.22 | 20.34 ± 0.23 | 21.66 ± 0.48 | 20.47 ± 0.34 | 18.81 ± 0.39 |
| CS-A (200 mg/kg) | 6/7 | 20.98 ± 0.54 | 18.62 ± 1.00 | 19.58 ± 0.94 | 19.98 ± 0.86 | 20.90 ± 1.02 |
| CS-E (200 mg/kg) | 7/7 | 21.53 ± 0.26 | 19.23 ± 0.72 | 19.83 ± 0.68 | 20.03 ± 0.64 | 20.39 ± 0.29 |
| SEMI5 (200 mg/kg) | 7/7 | 22.90 ± 0.46 | 22.40 ± 0.55* | 23.29 ± 0.53* | 23.03 ± 0.49** | 22.63 ± 0.52** |

represents $p < 0.01$ vs. normal control group.
*represents $p < 0.05$, and
**represents $p < 0.01$ vs. CIA model group.

TABLE 10

Effects of different drugs on the joint index scores of mice

| Group | Number of cases End/Start | 35 d | 38 d | 42 d | 45 d |
|---|---|---|---|---|---|
| Normal control group | 7/7 | 0.00 ± 0.00 | 0.00 ± 0.00 | 0.00 ± 0.00 | 0.00 ± 0.00 |
| CIA model group | 6/7 | 7.83 ± 1.11## | 8.00 ± 1.37## | 8.17 ± 1.56## | 9.83 ± 1.33## |
| Positive drug group (0.25 mg/kg) | 7/7 | 0.29 ± 00.29** | 1.29 ± 00.64** | 0.29 ± 00.29** | 0.86 ± 00.59** |
| CS-A (200 mg/kg) | 6/7 | 9.17 ± 2.17 | 8.50 ± 2.17 | 8.83 ± 2.57 | 8.17 ± 2.64 |
| CS-E (200 mg/kg) | 7/7 | 6.57 ± 1.70 | 7.29 ± 1.99 | 9.14 ± 1.83 | 8.86 ± 1.65 |
| SEMI5 (200 mg/kg) | 7/7 | 2.43 ± 0.99** | 2.86 ± 1.06* | 3.71 ± 1.15* | 5.43 ± 1.17* |

represents $p < 0.01$ vs. normal control group.
*represents $p < 0.05$, and
**represents $p < 0.01$ vs. CIA model group. A value is expressed as "mean ± sem".

TABLE 11

Test results of bone density of mouse toes

| Group | Number of cases End/Start | Bone density ($g/cm^3$) mean ± sem |
|---|---|---|
| Normal control group | 7/7 | 5262.0 ± 233.3 |
| CIA model group | 6/7 | 3131.0 ± 194.4## |
| Positive drug group (0.25 mg/kg) | 7/7 | 4089.0 ± 206.1* |
| CS-A (200 mg/kg) | 6/7 | 3759.0 ± 61.6* |
| CS-E (200 mg/kg) | 7/7 | 2852.0 ± 669.8 |
| SEMI5 (200 mg/kg) | 7/7 | 4581.0 ± 156.6** |

The bone density was measured in an area within 1.00 mm to a joint.
represents $p < 0.01$ vs. normal control group.
*represents $p < 0.05$, and
**represents $p < 0.01$ vs. CIA model group.

It can be seen from the comparison results of body weights of mice at the end in Table 9 that the SEMI5 drug exhibited a significant restoration effect on weight loss of mice. It can be seen from Table 10 that joints of mice usually began to swell at 4 w, developing from toes to soles and even ankle joints, and experienced a lesion peak at 5 w to 6 w, with a modeling rate of 100%. The SEMI5 drug significantly improved the joint swelling. It can be seen from Table 11 that the SEMI5 drug showed a significant improvement effect on bone density, which was superior to the positive drug. The above results indicate that the semi-synthetic SEMI5 drug has an anti-RA activity.

Experimental Example 5

The Glycan 3 (referred to as SEMI5) prepared in Example 3 was evaluated on anti-papain-induced OA models, specifically as follows:

I. Materials and Methods:

1. Animals:

SD rats, male (180 g to 220 g); 6 mice per group, which were purchased from Beijing Vital River Laboratory Animal Technology Co., Ltd., with license No.: SCXK (Beijing) 2012-0001.

2. Groups:

(1) Normal control group (Con group): intragastrically administered with DDW.

(2) Model group (Mod group): intragastrically administered with DDW.

(3) Positive drug celecoxib group (Pos group): the drug was purchased from Pfizer (W47055), formulated with DDW, stored at 4° C., and intragastrically administered once a day.

(4) Compound SEMI5 at a low dosage group (5L group): 50 mg/kg, which was formulated with DDW, stored at 4° C., and intragastrically administered once a day.

(5) Compound SEMI5 at a medium dosage group (5M group): 100 mg/kg, which was formulated with DDW, stored at 4° C., and intragastrically administered once a day.

(6) Compound SEMI5 at a high dosage group (5H group): 200 mg/kg, which was formulated with DDW, stored at 4° C., and intragastrically administered once a day.

II Experimental Results

1. Net Width of Knee Joints

A vernier caliper was used to measure the width of a skin-free and fat-free knee joint. The swelling degree of the joint could be visually measured.

TABLE 12

Net width of knee joint in each of the groups

| Group | Number of cases End/Start | Width of knee joint (cm) |
|---|---|---|
| Normal control group | 6/6 | 8.55 ± 0.08 |
| OA model group | 6/6 | 9.07 ± 0.15** |
| Positive drug group | 6/6 | 8.75 ± 0.11 |
| 5L | 6/6 | 8.53 ± 0.09## |
| 5M | 6/6 | 8.48 ± 0.06## |
| 5H | 6/6 | 8.49 ± 0.07## |

Notes:

As compared with animals in the normal control group (Con), animals in the model group (Mod) had knee joints with a significantly increased net width, with statistically significant difference. It suggests that the joints of animals in the model group were obviously swollen. There was no statistically significant difference between the positive drug group (Pos) and the model group. In terms of the net width of knee joints, animals in each of the administration groups showed a statistically significant difference from that in the model group (Mod). It suggests that the compound had a prominent anti-inflammatory activity.

**$p < 0.01$ vs. Con;

$p < 0.01$ vs. Mod.

2. Magnetic Resonance Imaging Results

Figure 8:
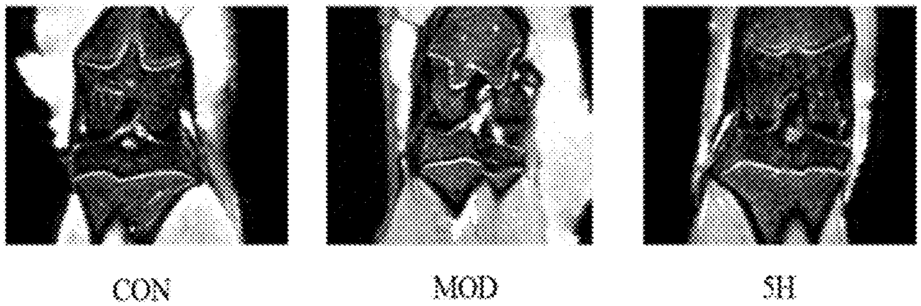
FIG. 8 shows magnetic resonance imaging (MRI) images of the knee joints of rats in different groups in Experimental Example 5. Note.
Figure 9:
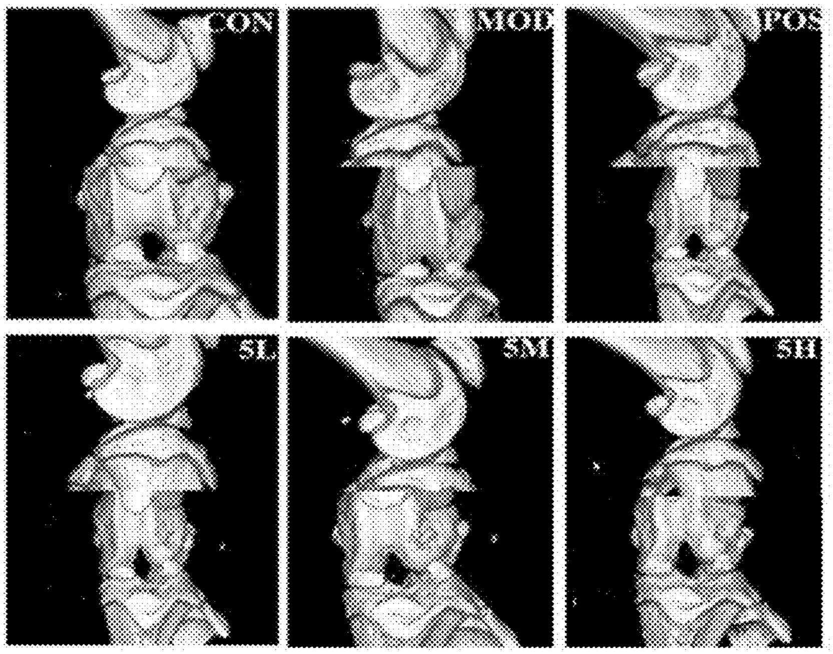
FIG. 9 shows computed tomography (CT) images of the knee joints of rats in different groups in Experimental Example 5. Note.

The damage degree of rat knee articular cartilage was detected by magnetic resonance imaging (as shown in FIG. 8). The data of change in a cartilage gray value as measured were calculated under respective conditions, which indicates a water content of articular cartilage in each of the groups. The higher the water content was, the closer was the condition of the articular cartilage to a normal physiological status (as shown in Table 13).

TABLE 13

Gray values of knee joints (n = 6)

| Group | Gray value |
|---|---|
| Normal control group | 20.54 ± 2.90 |
| OA model group | 8.12 ± 0.53** |
| 5H | 14.33 ± 1.67## |

It can be seen from Table 13 that, in terms of the gray value, animals in the model group (Mod) showed a statistically significant difference from that in the normal control group (Con). It suggests that an obvious cartilage destruction and a successful modeling. In terms of the gray value, animals in the high dosage administration group showed a statistically significant difference from that in the model group (Mod). The above results suggest that the cartilage was heavily damaged in the model group, while the administration group showed a significant improvement effect. **p<0.01 vs Con; ##p<0.01 vs Mod.

3. CT Test Results

A subchondral bone of the rat knee joint can be detected by CT to determine the remodeling of the subchondral bone.

III. Experimental Conclusions

1. Pharmacodynamic evaluation on anti-DSS-induced acute ulcerative colitis models 1) Animals in the UC model group showed significant body weight loss, hematochezia, watery stools, colon contracture, and increase of DAI complex index scores and colon histopathological scores, indicating a success modeling of DSS-induced ulcerative colitis model of mice. The system is reliable and suitable for evaluating the activities of anti-UC compounds.

2). The SASP group failed to effectively alleviate the body weight loss of UC model animals in this experiment, but improved the phenomena such as watery stools, hematochezia, and colon contracture in UC model animals. It indicates that SASP exhibited a certain anti-UC activity.

3). The SEMI5-50 group could effectively alleviate the body weight loss of model animals, and exhibited certain anti-UC activities in respects such as watery stools, hematochezia, reduction of DAI scores and the like in UC model animals, with statistically significant difference. The above results show that, in the test system, the SEMI5-50 exhibited a significant therapeutic effect on the DSS-induced UC animal models.

4). The SEMI5-150 group failed to alleviate the body weight loss of UC model animals with any statistically significant difference, but could improve the colon contracture with a statistically significant difference, and exhibited anti-UC activities in aspects such as watery stools, hematochezia, and reduction of DAI and histological scores in UC model animals with a statistically-significant difference. The above results show that, in the test system, the SEMI5-150 exhibited a certain therapeutic effect on the DSS-induced UC animal models.

2. Pharmacodynamic evaluation on anti-type I protein-induced toe swelling mouse models 1). It can be known from the comparison results of body weights of mice at the end that the SEMI5 exhibited a significant restoration effect on the weight loss of arthritis mice.

2). The SEMI5 showed a significant improvement effect on joint swelling.

3). The SEMI5 showed a significant improvement effect on articular bone density, which was superior to the improvement effect of the positive drug. The above results indicate that the semi-synthetic SEMI5 has anti-RA activity.

3. Pharmacodynamic evaluation on anti-papain-induced osteoarthritis rat models

1). As compared with animals in the normal control group (Con), animals in the model group (Mod) had knee joints with a significantly increased net width, with statistically-significant difference. It suggests that the joints of animals in the model group were obviously swollen. There was no statistically significant difference between the positive drug group (Pos) and the model group. In terms of the net width of knee joints, animals in each of the administration groups showed a statistically significant difference from that in the model group (Mod), suggesting that the SEMI5 exhibited a superior anti-inflammatory activity.

2). The CON group showed a normal joint space, an intact and undamaged articular cartilage surface, a normal subchondral bone, a normal cartilage thickness, an appropriate amount of subpatellar fat, a synovial membrane, and a little synovial fluid. The MOD group showed a narrowed joint space, a damaged or even lost articular cartilage surface, an incomplete outer cartilage edge, an unclear cartilage shape, and a decreased cartilage thickness. The SEMI5H group showed a clear joint shape, a restored joint space, and a little synovial fluid.

3). In terms of the gray value, animals in the model group (Mod) showed a statistically significant difference from that in the normal control group (Con), suggesting an obvious cartilage destruction and a successful modeling. In terms of the gray value, animals in the high-dosage SEMI5 group showed a statistically significant difference from that in the model group (Mod). The above results suggest that the cartilage was heavily damaged in the model group and the administration group showed a significant improvement effect.

4). As compared with the shape of the normal rat knee joint shape in the CON group, the MOD model group showed a bone destruction and severe erosion in the subchondral bone of the knee joints, formation of obvious cavities at the joints, and deformation of bone joints. The POS positive drug and SEMI5L groups showed less bone destruction and erosion than the model group. The SEMI5M and SEMI5H groups showed a significantly improved bone destruction and erosion as compared with the model group.

The above results indicate that the semi-synthetic SEMI5 has an anti-OA activity.

The above descriptions are merely preferred embodiments of the present disclosure. It is to be noted that a person of ordinary skill in the art may make certain improvements and modifications without departing from the principle of the present disclosure. Such improvements and modifications should be deemed as falling within the protection scope of the present disclosure.

The invention claimed is:

1. A metal salt of chondroitin sulfate glycan having formula (I):

(I)

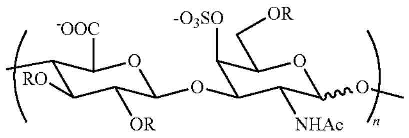

R = H or $SO_3^-$ which is electrically neutral, and comprises a chondroitin sulfate glycan anion and a metal cation; wherein the chondroitin sulfate glycan anion has an average molecular weight in a range of from 4,000 Da to 15,000 Da;

the chondroitin sulfate glycan anion has a molar ratio of $—SO_3^-$ to $—COO^-$ in a range of from 1.9 to 2.5;

n for the chondroitin sulfate glycan anion is within a range of 6≤n≤45; and in the formula (I), at least one of the R groups at 2- and 3-positions of glucuronic acid (GlcA) is $SO_3^-$.

2. The metal salt of chondroitin sulfate glycan according to claim 1, wherein the metal cation comprises a sodium ion and/or a calcium ion and/or a potassium ion.

3. A method for preparation of the metal salt of chondroitin sulfate glycan according to claim 1, comprising steps of:

mixing a raw material of chondroitin sulfate glycan, a sulfating reagent, and an organic solvent for sulfation to provide a sulfation product system; and subjecting the sulfation product system successively to a first precipitating treatment, salification treatment, dialysis, a second precipitating treatment, and gel column purification to provide the metal salt of chondroitin sulfate glycan, wherein a salifying reagent used in the salification treatment is an aqueous metal hydroxide solution wherein the raw material of chondroitin sulfate glycan comprises a chondroitin sulfate glycan A and a chondroitin sulfate glycan C; wherein the chondroitin sulfate glycan A has a content in a range of from 70% to 90% by weight, and the chondroitin sulfate glycan C has a content in the range of from 10% to 30% by weight.

4. The method for preparation according to claim 3, wherein the sulfating reagent comprises one or more selected from the group consisting of sulfur trioxide trimethylamine complex, sulfur trioxide pyridine complex, and sulfur trioxide triethylamine complex; and an equivalent ratio of the sulfating reagent to the repeating disaccharide units in the raw material of chondroitin sulfate glycan is in a range of (1-10):1.

5. The method for preparation according to claim 4, wherein the sulfation is performed at a temperature in a range of from 40° C. to 120° C. for a period of time of from 2 h to 36 h; and an equivalent ratio of the sulfating reagent to the repeating disaccharide units in the raw material of chondroitin sulfate glycan is in a range of (3-8):1.

6. The method for preparation according to claim 3, wherein the salifying reagent is an aqueous sodium hydroxide solution and/or an aqueous potassium hydroxide solution;

and the salifying reagent has a concentration in a range of from 1 mol/L to 4 mol/L.

7. The method for preparation according to claim 3, wherein a first precipitating reagent used in the first precipitating treatment is an aqueous ethanol solution with a volume fraction in a range of from 90% to 95%;

a second precipitating reagent used in the second precipitating treatment is ethanol; and a dialysis bag used in the dialysis has a molecular weight cut-off in a range of from 3,000 Da to 12,000 Da.

8. A pharmaceutical composition, wherein the pharmaceutical composition comprises the metal salt of chondroitin sulfate glycan according to claim 1 and a pharmaceutically acceptable carrier or excipient.

9. A method for treating an inflammatory disease comprising administrating a pharmaceutical composition comprising the metal salt of chondroitin sulfate glycan according to claim 1 to a subject in need thereof.

10. The method according to claim 9, wherein the inflammatory disease is ulcerative colitis, osteoarthritis, or rheumatoid arthritis.

* * * * *